(12) United States Patent
Wu et al.

(10) Patent No.: US 8,278,486 B2
(45) Date of Patent: Oct. 2, 2012

(54) PROCESS AND INTERMEDIATES FOR THE PREPARATION OF N-ACYLATED-4-ARYL BETA-AMINO ACID DERIVATIVES

(75) Inventors: Shulin Wu, Plainsboro, NJ (US); Bo Yu, Jiangsu (CN); Yejing Wang, Jiangsu (CN); Alain Delice, Willingboro, NJ (US); Jingyang Zhu, Monmouth Junction, NJ (US)

(73) Assignee: Chiral Quest, Inc., Monmouth Junction, NJ (US)

( * ) Notice: Subject to any disclaimer, the term of this patent is extended or adjusted under 35 U.S.C. 154(b) by 64 days.

(21) Appl. No.: 12/650,128

(22) Filed: Dec. 30, 2009

(65) Prior Publication Data
US 2010/0280245 A1    Nov. 4, 2010

Related U.S. Application Data

(60) Provisional application No. 61/142,037, filed on Dec. 31, 2008.

(51) Int. Cl.
*C07C 239/00* (2006.01)

(52) U.S. Cl. ........................................ 564/193

(58) Field of Classification Search .............. 564/193
See application file for complete search history.

(56) References Cited

U.S. PATENT DOCUMENTS

| 7,125,873 | B2 | 10/2006 | Edmondson et al. | |
|---|---|---|---|---|
| 2004/0186314 | A1 | 9/2004 | Malan et al. | |
| 2009/0192326 | A1* | 7/2009 | Perlman et al. | 560/37 |

FOREIGN PATENT DOCUMENTS

| WO | 03/004498 | A1 | 1/2003 |
|---|---|---|---|
| WO | 2004/085378 | A1 | 10/2004 |
| WO | 2004/085661 | A2 | 10/2004 |
| WO | 2004/087650 | A2 | 10/2004 |
| WO | 2006/081151 | A1 | 8/2006 |
| WO | 2009/064476 | A1 | 5/2009 |

* cited by examiner

*Primary Examiner* — James O Wilson
*Assistant Examiner* — Douglas M Willis
(74) *Attorney, Agent, or Firm* — Fox Rothschild LLP; Peter J. Butch, III; Robert N. Henrie, II

(57) ABSTRACT

A process for producing an enantiomerically enriched compound of Formula I:

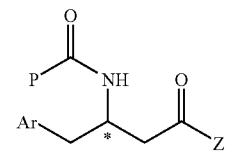

I where the R-configuration, or S-configuration at the stereogenic center is marked with an *; by hydrogenating an enamide of formula III:

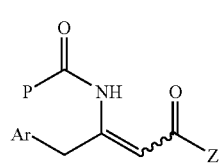

III in an organic solvent in the presence of a catalyst comprising a transition metal selected from rhodium or iridium, complexed to a chiral diphosphine ligand;
Ar is optionally substituted phenyl;
Z is $OR^1$, $SR^1$ or $NR^1R^2$; and P is $R^3$, $OR^3$ or $NR^3R^4$;
$R^1$ and $R^2$ are selected from H, $C_{1-8}$ alkyl, $C_{5-12}$ cycloalkyl, aryl and aryl-$C_{1-2}$-alkyl; or $R^1$ and $R^2$ together with the nitrogen atom form a $C_{4-7}$-membered heterocyclic ring optionally fused with a 5- to 6-membered carbocyclic or heterocyclic ring; and
$R^3$ and $R^4$ are selected from H, $C_{1-8}$ alkyl, aryl, $C_{5-12}$ cycloalkyl and aryl-$C_{1-2}$-alkyl; or $R^3$ and $R^4$ together with the nitrogen atom form a $C_{4-7}$-membered heterocyclic ring.

16 Claims, 1 Drawing Sheet

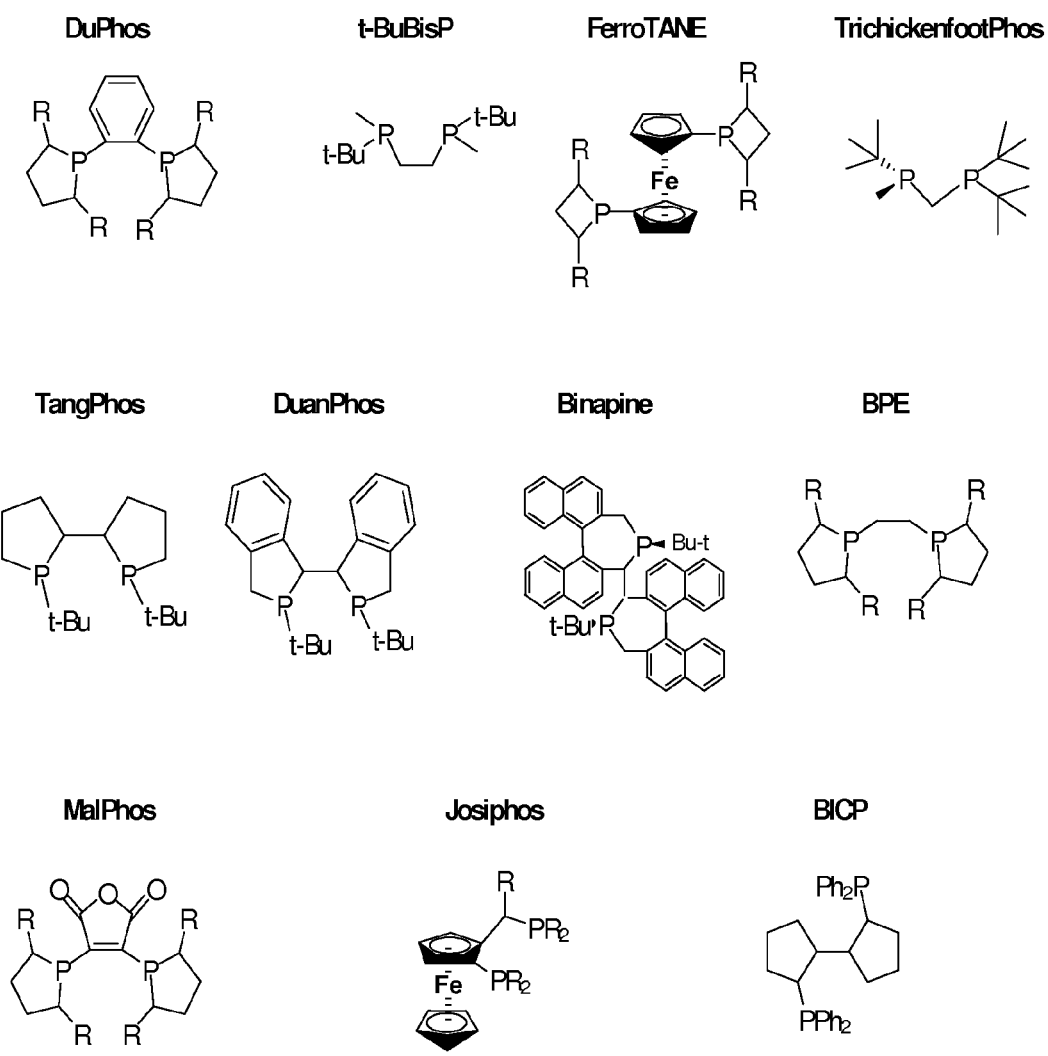

US 8,278,486 B2

PROCESS AND INTERMEDIATES FOR THE PREPARATION OF N-ACYLATED-4-ARYL BETA-AMINO ACID DERIVATIVES

CROSS-REFERENCE TO RELATED APPLICATIONS

This application claims the benefit under 35 U.S.C. 119(e) of U.S. Provisional Application Ser. No. 61/142,037 filed on Dec. 31, 2008.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention relates to a process for producing enantiomerically enriched beta-amino acid derivatives which are important chiral building blocks and intermediates in pharmaceuticals. More specifically, the invention pertains to a novel process for practically, conveniently and economically producing enantiomerically enriched beta-amino acid derivatives which are useful for the synthesis of amide inhibitors of dipeptidyl peptidase-IV, which have been used to treat Type 2 diabetes.

2. Description of Related Art

The present invention provides a process for producing enantiomerically enriched beta-amino acid derivatives represented by the following general structural formula I, or its corresponding pharmaceutically acceptable salts, having the R-configuration at the stereogenic center marked with an *;

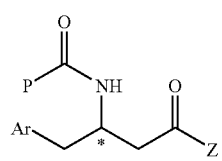

I wherein Ar is phenyl, which is unsubstituted or substituted with one to five substituents independently selected from halogen, trifluoromethyl and trifluoromethoxy; Z is $OR^1$, $SR^1$ and $NR^1R^2$; and P is $R^3$, $OR^3$, and $NR^3R^4$;

$R^1$ and $R^2$ are each independently H, $C_{1-8}$ alkyl, $C_{5-12}$ cycloalkyl, aryl, or aryl-$C_{1-2}$ alkyl; or $R^1$ and $R^2$ together with the nitrogen atom to which they are attached form a $C_{4-7}$ member heterocyclic ring system optionally containing an additional heteroatom selected from O, S, and N—$C_{1-4}$ alkyl, said heterocyclic ring system being optionally fused with a 5- to 6-member saturated, unsaturated or aromatic carbocyclic ring system or a 5- to 6-member saturated, unsaturated or aromatic heterocyclic ring system containing one to two heteroatoms selected from O, S, and N—$C_{1-4}$ alkyl, wherein the fused ring system is unsubstituted or substituted with one to two substituents independently selected from hydroxyl, amino, fluoro, $C_{1-4}$ alkyl, $C_{1-4}$ alkoxy and trifluoromethyl; and $R^3$ and $R^4$ are each independently H, $C_{1-8}$ alkyl, $C_{5-12}$ cycloalkyl, aryl, or aryl-$C_{1-2}$ alkyl; or $R^3$ and $R^4$ together with the nitrogen atom to which they are attached form a $C_{4-7}$ member heterocyclic ring system optionally containing an additional heteroatom selected from O, S, and N—$C_{1-4}$ alkyl.

As disclosed in WO 03/004498, the Formula I compounds are important precursors for the synthesis of amide inhibitors of dipeptidyl peptidase-IV (general structure II), which are commercially available as drugs used to treat Type 2 diabetes (trade name, Sitagliptin, JANUVIA™)

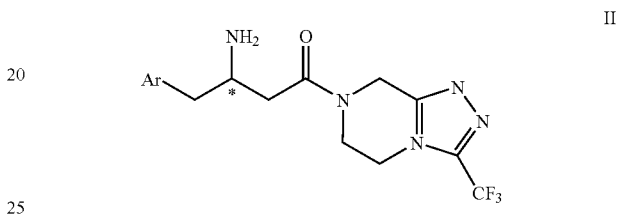

II

As disclosed in WO 03/004498 and WO 04/087650, the amide inhibitors of dipeptidyl peptidase-IV are prepared by standard peptide coupling of a beta amino acid with fused heterocycles. However, a large number of synthetic steps required to prepare the beta amino acids, which make the processes unpractical.

Other routes (WO 2004/085661, WO 2004/085378 and WO 2006/081151) involve hydrogenation of enamine derivatives with a chiral auxiliary or asymmetric hydrogenation of an N-unprotected enamine in the presence of a rhodium catalyst and Joshiphos ligand. However, high catalyst loading or use of special solvents makes the processes not cost-efficient.

As disclosed in WO 2009/064476, the key intermediate beta amino acid was prepared via asymmetric hydrogenation of an N-Boc protected enamine with BINAP-$RuCl_2$ as the catalyst. However, even with long reaction time (40 h) and elevated temperature (80° C.), 24.0% of the starting material was recovered. Furthermore, a low enantiomeric excess (ee) was afforded.

There remains a need for practical methods by which beta amino acids may be synthesized, especially those useful in the synthesis of amide inhibitors of dipeptidyl peptidase-IV.

BRIEF SUMMARY OF THE INVENTION

The present invention addresses this need. The present invention provides a process for the preparation of chiral beta amino acid derivatives of structural formula I in an efficient enantioselective fashion through transition metal-catalyzed asymmetric hydrogenation of a prochiral enamide of structural formula III:

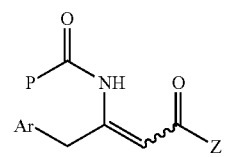

III in the presence of a transition metal precursor complexed to a chiral phosphine ligand.

Accordingly, one aspect of the present invention provides a process for producing enantiomerically enriched beta-amino acid derivatives represented by the structure of Formula I, having the R- or S-configuration at the stereogenic center marked with an *;

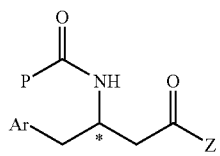

I wherein Ar is phenyl, which is unsubstituted or substituted with one to five substituents independently selected from halogen, trifluoromethyl and trifluoromethoxy; Z is $OR^1$, $SR^1$ and $NR^1R^2$; and P is $R^3$, $OR^3$, and $NR^3R^4$;

$R^1$ and $R^2$ are each independently H, $C_{1-8}$ alkyl, $C_{5-12}$ cycloalkyl, aryl, or aryl-$C_{1-2}$ alkyl; or $R^1$ and $R^2$ together with the nitrogen atom to which they are attached form a $C_{4-7}$ member heterocyclic ring system optionally containing an additional heteroatom selected from O, S, and N—$C_{1-4}$ alkyl, said heterocyclic ring system being optionally fused with a 5- to 6-member saturated, unsaturated or aromatic carbocyclic ring system or a 5- to 6-member saturated, unsaturated or aromatic heterocyclic ring system containing one to two heteroatoms selected from O, S, and N—$C_{1-4}$ alkyl, wherein the fused ring system is unsubstituted or substituted with one to two substituents independently selected from hydroxyl, amino, fluoro, $C_{1-4}$ alkyl, $C_{1-4}$ alkoxy and trifluoromethyl; and $R^3$ and $R^4$ are each independently H, $C_{1-8}$ alkyl, $C_{5-12}$ cycloalkyl, aryl, or aryl-$C_{1-2}$ alkyl; or $R^3$ and $R^4$ together with the nitrogen atom to which they are attached form a $C_{4-7}$ member heterocyclic ring system optionally containing an additional heteroatom selected from O, S, and N—$C_{1-4}$ alkyl; wherein the process asymetrically hydrogenates a compound having the structure of Formula III in the presence of a transition metal precursor complexed to a chiral phosphine ligand.

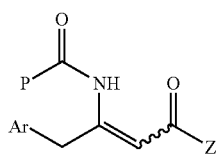

III

According to one embodiment of this aspect of the invention, the chiral phosphine ligands have a structure according to Formula IV:

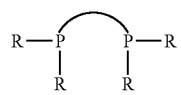

IV wherein each R is independently $C_{1-8}$ alkyl, $C_{3-8}$ cycloalkyl or aryl, and P is phosphorus.

According to another embodiment of this aspect of the invention, the transition metal precursor is selected from [M(monoolefin)$_2$ acetylacetonate], [M(diolefin)acetyl-acetonate], [M(monoolefin)$_4$]X and [M(diolefin)$_2$]X, wherein X is a noncoordinating anion selected from methanesulfonate trifluoromethanesulfonate, tetrafluoroborate, hexa-fluorophosphate and hexafluoroantimonate, and M is rhodium or iridium; and [M(arene)Cl$_2$]$_2$, [M(diolefin)Cl$_2$]n and [M(diolefin)($\eta^3$-2-methyl-1-propenyl)$_2$], wherein M is ruthenium. Preferably, the transition metal precursor is [rhodium(COD)$_2$]X or [rhodium(NBD)$_2$]X.

According to another embodiment of this aspect of the invention, the catalytic complex of the transition metal precursor and the chiral diphosphine ligand used in the hydrogenation process of the present invention may be generated in situ by addition of the transition metal species and the chiral diphosphine ligand to the reaction system. According to an alternative embodiment of this aspect of the invention, the catalytic complex of the transition metal precursor and the chiral diphosphine ligand used in the hydrogenation process of the present invention may be preformed with or without isolation and then added to the reaction system. The preformed complex is represented by the formula:

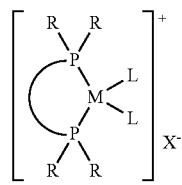

wherein X is the same non-coordinating anion described above, and L is a neutral ligand such as an olefin, and preferably a chelating diolefin such as 1,5-cyclooctadiene or norbornadiene, M, R, and P are the same as above in Formula IV. According to another embodiment of this aspect of the invention, the beta enamine compounds with the structure of Formula III to be asymmetrically hydrogenated by the method of the present invention are prepared from enamine derivatives represented by the structure of Formula V (wherein the amino group is unprotected):

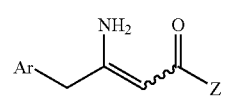

V by reaction with an acylation reagent in the presence of a suitable organic base. Examples of suitable acylation reagents include $C_{2-8}$-alkyl-, aryl- and aryl-$C_{1-2}$-alkyl-acyl chlorides, anhydrides and chloroformates such as acetyl chloride, acetic anhydride, Boc anhydride and benzyl chloroformate.

Another inspect of the present invention provides amide inhibitors of dipeptidyl peptidase-IV (general structure II) prepared by the process of the present invention, followed by a deprotective procedure.

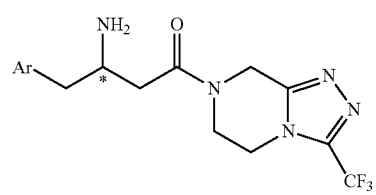

II

In another aspect of the present invention, structurally novel intermediates used in the process of the present invention are provided, which are useful in the preparation of compounds having the structure of Formula II. That is, compounds are provided having the structure of Formula III:

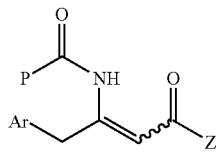

III

Wherein Ar is phenyl which is unsubstituted or substituted with one to five substituents independently selected from halogen, trifluoromethyl and trifluoromethoxy;

Z is $OR^1$, $SR^1$ and $NR^1R^2$; and P is $R^3$, $OR^3$, and $NR^3R^4$;

$R^1$ and $R^2$ are each independently selected from H, $C_{1-8}$ alkyl, aryl, $C_{5-12}$ cycloalkyl and aryl-$C_{1-2}$-alkyl; or $R^1$ and $R^2$ together with the nitrogen atom to which they are attached form a $C_{4-7}$-member heterocyclic ring system optionally containing an additional heteroatom selected from O, S, and N—$C_{1-4}$-alkyl, said heterocyclic ring system being optionally fused with a 5- to 6-member saturated, unsaturated or aromatic carbocyclic ring system or a 5- to 6-member saturated, unsaturated or aromatic heterocyclic ring system containing one to two heteroatoms selected from O, S, and N—$C_{1-4}$-alkyl, said fused ring system being unsubstituted or substituted with one to two substituents independently selected from hydroxyl, amino, fluoro, $C_{1-4}$ alkyl, $C_{1-4}$ alkoxy and trifluoromethyl; and $R^3$ and $R^4$ are each independently selected from H, $C_{1-8}$ alkyl, $C_{5-12}$ cycloalkyl, aryl and aryl-$C_{1-2}$-alkyl; or $R^3$ and $R^4$ together with the nitrogen atom to which they are attached form a $C_{4-7}$-member heterocyclic ring system optionally containing an additional heteroatom selected from O, S, and N—$C_{1-4}$-alkyl.

According to one embodiment of this aspect of the invention, Ar is 2,4,5-tri-fluorophenyl or 2,5-difluorophenyl. According to another embodiment of this aspect of the invention, P is $R^3$ and $R^3$ is H, $C_{1-8}$ alkyl or aryl. According to another embodiment of this aspect of the invention, P is $OR^3$ and $R^3$ is tert-butyl or an optionally substituted benzyl group.

According to yet another embodiment of this aspect of the invention, Z is $OR^1$ or $NR^1R^2$. In a more specific embodiment Z as $NR^1R^2$ is a heterocycle with the structure of Formula VI:

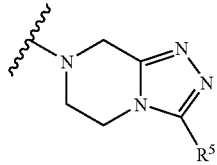

VI wherein $R^5$ is H, or $C_{1-4}$ alkyl which is unsubstituted or substituted with one to five fluorines and preferably trifluoromethyl.

A more complete appreciation of the invention and many more other intended advantages can be readily obtained by reference to the following detailed description of the preferred embodiment.

BRIEF DESCRIPTION OF THE DRAWING

FIG. 1 depicts the structures for chiral optically active phosphine ligands BICP, DuPhos, t-BuBisP*, BPE, FerroTANE, MalPhos, TrichickenPhos, TangPhos, DuanPhos, Binapine and JosiPhos, wherein each R is independently $C_{1-8}$ alkyl, $C_{3-8}$ cycloalkyl or aryl, and P is phosphorous.

DETAILED DESCRIPTION OF THE INVENTION

Throughout the present invention, the following terms have the indicated meaning:

The term "enantiomerically enriched compound" means optically active compounds with an enantiomeric excess (ee) of greater than 20%. The term "enantiomerically pure compound" means optically active compounds with an ee of greater than 99%. The term "enantiomerically enriched and essentially pure compound" means optically active compound with an ee of greater than about 95% but less than about 99%.

The term "alkyl groups" means an alkyl group of the designated length in either a linear or branched configuration. Exemplary of such alkyl groups are methyl, ethyl, propyl, isopropyl, butyl, sec-butyl, tert-butyl, pentyl, isopentyl, hexyl, isohexyl, and the like. The alkyl groups are unsubstituted or substituted with one to three groups independently selected from halogen, hydroxy, carboxy, aminocarbonyl, amino, $C_{1-4}$ alkoxy and $C_{1-4}$ alkylthio.

The term "cycloalkyl" means a cycloaliphatic group of five to twelve total carbon atoms, or any number within this range, for example, cyclopentyl, cyclohexyl, cycloheptyl, cyclooctyl and the like.

The term "aryl" means an aromatic group, preferably phenyl or naphthyl with zero to five substituents independently selected from halogen, hydroxyl, amino, $C_{1-4}$ alkyl, alkoxyl, trifluoromethyl. The term "arene" means benzene, naphthene and o-, m-, or p-isopropyltoluene.

The term olefin means an acyclic or cyclic hydrocarbon containing one or more double bonds including aromatic cyclic hydrocarbons. The term includes, but not limited to, 1,5-cyclooctadiene (COD) and norbornadiene (NBD).

The term "heteroaryl" means a 5- or 6-member aromatic heterocycle that contains at least one ring heteroatom selected from O, S and N. Heteroaryls also include heteroaryls fused to other kind of rings, such as aryl, cycloalkly and heterocycles that are not aromatic. Heteroaryls include, but are not limited to, pyrrolyl, isoxazolyl, isothiazolyl, pyrazolyl, pyridinyl, oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuryl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, and dibenzofuranyl. Heteroaryls may be unsubstituted or substituted with one to five substituents independently selected from halogen, hydroxyl, amino, $C_{1-4}$ alkyl, alkoxy and trifluoromethyl.

The present invention provides a process for producing enantiomerically enriched beta-amino acid derivatives represented by the structure of Formula I, having the R-, or S-configuration at the stereogenic center marked with an wherein Ar, P and Z are the same as described above with respect to Formula I.

The process asymmetrically hydrogenates an enamide precursor with the structure of Formula III:

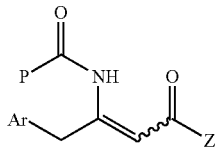

in a suitable organic solvent in the presence of a transition metal precursor complexed to a chiral phosphine ligand.

Preferably, the chiral phosphine ligand is a diphosphine ligand represented by the structural formula IV:

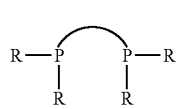

wherein each R is independently $C_{1-8}$ alkyl, $C_{3-8}$ cycloalkyl or aryl, and P is phosphorous.

Examples of suitable chiral optically active phosphine ligands include, but are not limited to BICP, DuPhos, t-BuBisP*, BPE, FerroTANE, MalPhos, TrichickenPhos, TangPhos, DuanPhos, Binapine and JosiPhos as shown in FIG. 1, wherein each R is independently $C_{1-8}$ alkyl, $C_{3-8}$ cycloalkyl or aryl, and P is phosphorus.

Because these optically active phosphine ligands occur with (R)- or (S)-configurations, one configuration may be selected over the other depending on the desired absolute configuration of the Formula I compound to be prepared. It is possible to control the configuration of the hydrogenation products by the judicious choice of the configuration of the diphosphine ligand.

The catalytic complex of the transition metal precursor and the chiral diphosphine ligand used in the hydrogenation process of the present invention may be either (a) generated in situ by addition of the transition metal species and the chiral diphosphine ligand to the reaction system, or (b) pre-formed with or without isolation and then added to the reaction system. The preformed complex is represented by the formula:

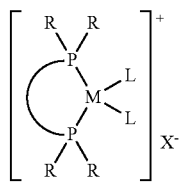

wherein X ix a non-coordinating anion, such as methanesulfonate trifluoromethane-sulfonate, tetrafluoroborate, hexafluorophosphate and hexafluoroantimonate, L is a neutral ligand such as an olefin, and preferably a chelating diolefin such as 1,5-cyclo-octadiene or norbornadiene), M is rhodium iridium, or ruthenium, and P is phosphorus.

Examples of transition metal precursors include [M(monoolefin)$_2$acetyl-acetonate], [M(diolefin)acetylacetonate], [M(monoolefin)$_4$]X and [M(diolefin)$_2$]X, wherein X is a non-coordinating anion selected from methanesulfonate trifluoromethane-sulfonate, tetrafluoroborate, hexafluorophosphate and hexafluoroantimonate, and M is rhodium or iridium; and [M(arene)Cl$_2$]$_2$, [M(diolefin)Cl$_2$]$_n$, and [M(diolefin)($\eta^3$-2-methyl-1-propenyl)$_2$], wherein M is ruthenium. Preferably, the transition metal precursor is [rhodium (COD)$_2$]X or [rhodium(NBD)$_2$]X.

The catalytic metal complex used in the asymmetric hydrogenation reaction in the present invention is used in amount of about 1/10000 to 1/10, preferably about 1/5000-1/100 mole, per mole of the substrate. The hydrogen pressure is in the range of about 15 psi to about 1500 psi, preferably about 45 psi to about 450 psi. The reaction temperature used for the hydrogenation is in the range of about 0° C. to about 100° C., preferably about 25 to 60° C.

The asymmetric hydrogenation in this invention is carried out in an organic solvent. Suitable organic solvents include aromatic hydrocarbons such as toluene, benzene and chlorobenzene, aliphatic esters such as ethyl acetate, propyl acetate and butyl acetate, ethers such as tert-butyl methyl ether, diisopropyl ether and tetrahydrofuran, halogenated hydrocarbons such as dichloromethane and dichloroethane, and alcohols such as methanol, ethanol and isopropanol. These can be used alone or as a mixture of two or more solvents. Preferably, the solvent is an ether such as tert-butyl methyl ether or tetrahydrofuran, or an alcohol such as methanol or ethanol.

Because of the nature of the restricted rotation of the carbon-carbon double bond, olefins such as the beta enamine compounds with the structure of Formula III occur with (Z)- or (E)-geometric isomers. The beta enamine compounds with the structure of Formula III for use in the asymmetric hydrogenation process of the present invention are intended to include ether (Z)- or (E)-geometric isomers, or the mixtures of the two isomers.

At least one aspect of the present invention requires that the final enantiomerically enriched compound to have an ee in the range of, for example, about 20% to about 99%. In yet another embodiment the compound may have an ee in the range of about 35% to 99%. In a preferred embodiment, the final compound would have an ee in the range of from about 40% to about 99%. In a more preferred embodiment, the final compound would have an ee in the range of about 45% to about 99% and in the most preferred embodiment, the enantiomerically enriched and essentially pure compound would have an ee greater than 95%. In one embodiment the enantiomerically enriched and essentially pure compound with the structure of Formula I is obtained with 97% ee. In another embodiment the enantiomerically pure compound with the structure of Formula I is obtained with 99% ee. In yet other embodiments, enantiomerically enriched compounds were obtained with a 37% or 42% ee.

The beta enamine compounds with the structure of Formula III to be asymmetrically hydrogenated by the method of the present invention can be prepared from enamine derivatives represented by the structure of Formula V (wherein the amino group is unprotected):

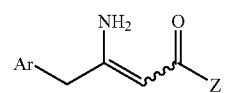

by reaction with an acylation reagent in the presence of a suitable organic base, wherein the acylation reagents are selected from $C_{2-8}$-alkyl-, aryl- and aryl-$C_{1-2}$-alkyl-acyl chlorides, anhydrides and chloroformates. Preferred acylation reagents include acetyl chloride, acetic anhydride, Boc anhydride and benzyl chloroformate.

Suitable organic bases include one or more compounds selected from triethyl amine, tributyl amine, diisopropylethylamine, dimethyl aniline, pyridine, N,N-dimethyl-4-amino pyridine (DMAP), 1.8-diazabicyclo[5.4.0]-7-undecen (DBU) and 1,4-diazabi-cyclo[2.2.2]octane (DABCO), with pyridine and DMAP being preferred.

The method for the preparation of the amino-unprotected enamine compounds having the structure of Formula V is known to those of ordinary skill in the art. For example, such compounds may include the structure of the Formula V described in the WO 04/085378.

The present invention will be further described in the following examples, which are not intended to limit this invention and can be modified within the scope of this invention. All parts and percentages are by weight unless otherwise noted and all temperatures are in degrees Celsius. Solvents were of HPLC grade and used without further purification.

EXAMPLES

Example 1

Methyl 4-(2,4,5-trifluorophenyl)acetoacetate

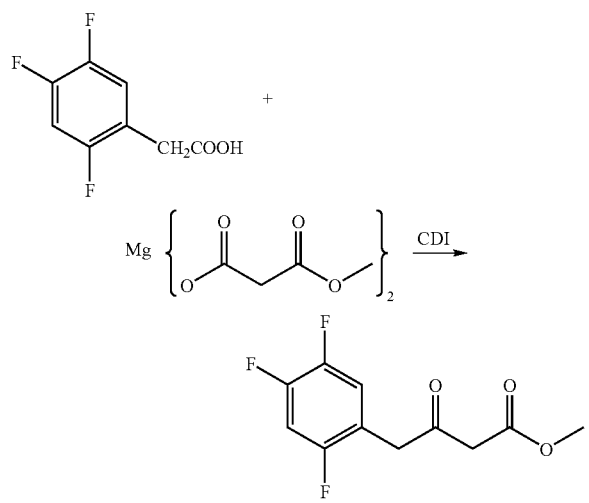

To a solution of 2,4,5-trifluorophenyl acetic acid (42.2 g, 222 mmol) in THF (400 mL) was added 1,1'-carbonyldiimidazole (39.5 g, 244 mmol) in portions at 0° C. The mixture was warmed to room temperature for 1 h, stirred at room temperature for another 1 h, and transferred to another flask containing 1.1 equivalent of methyl malonic acid magnesium salt. The stirring was continued for 24 h and quenched with 1N HCl. The mixture was extracted with dichloromethane and the organic phase was washed with saturated sodium bicarbonate, then brine, then dried over sodium sulfate, filtered and evaporated. The residue was crystallized from isopropanol/water to give 42.2 g (77.3%) of off-white solid. $^1$H NMR (300 MHz, CDCl$_3$) 7.10-6.90 (m, 2H), 3.85 (s, 2H), 3.78 (s, 3H), 3.55 (s, 2H)

Example 2

(Z)-methyl-3-amino-4-(2,4,5-trifluorophenyl)but-2-enoate

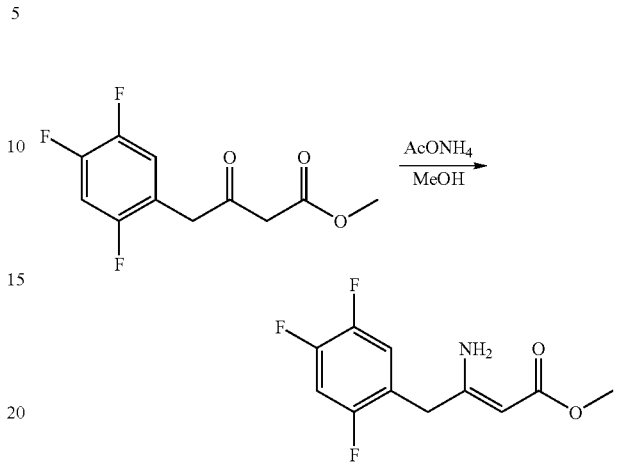

A mixture of methyl 4-(2,4,5-trifluorophenyl)acetoacetate from Example 1 (25.0 g, 102 mmol) and ammonium acetate (38.5 g, 500 mmol) in methanol (250 ml) was stirred at reflux until the starting material totally disappeared (~4 h). The whole reaction mixture was then concentrated, switched to dichloromethane and filtered. The filtration was washed with water, then brine, then dried over sodium sulfate, filtered and evaporated—ed. The residue oil solidified when hexane was added. The solid was collected by filtration and dried to give 22.4 g of the enamine product (89.6%). $^1$H NMR (300 MHz, CDCl$_3$) 7.12-7.03 (m, 1H), 6.99-6.90 (m, 1H), 4.56 (s, 1H) 3.65 (s, 3H), 3.40 (s, 2H)

Example 3

(Z)-Methyl-3-[N-(tert-butoxycarbonyl)amino]-4-(2,4,5-trifluorophenyl)but-2-enoate

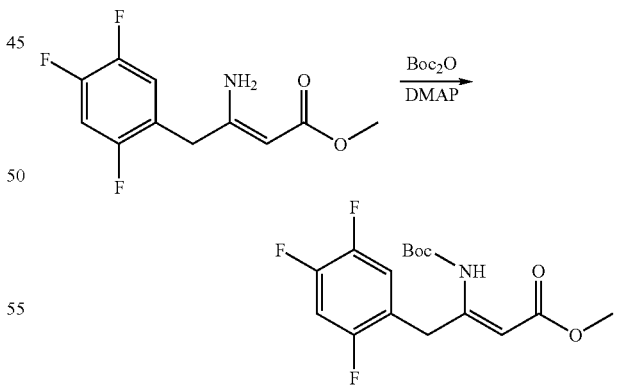

To a solution of (Z)-methyl-3-amino-4-(2,4,5-trifluorophenyl)but-2-enoate of Example 2 (1.95 g, 7.96 mmol) and DMAP (1.07 g, 8.76 mmol) in acetonitrile (20 mL) was added Boc anhydride (3.84 g, 17.6 mmol) in portions at 0° C. The reaction mixture was stirred at room temperature overnight, quenched with 1N HCl, and extracted with ethyl acetate (3×20 mL). The combined organic phase was washed with saturated sodium bicarbonate, then brine, then dried over sodium sulfate, filtered and evaporated. The oil residue was slurried with methanol to give a white solid (0.889 g, 32.4%). ¹H NMR (300 MHz, CDCl₃) 10.42 (s, 1H) 7.15-7.05 (m, 1H), 6.95-6.90 (m, 1H), 4.70 (s, 1H), 4.08 (s, 2H), 3.65 (s, 3H), 1.45 (s, 9H).

Example 4

(R)-Methyl-3-[N-(tert-butoxycarbonyl)amino]-4-(2,4,5-trifluorophenyl)butanoate

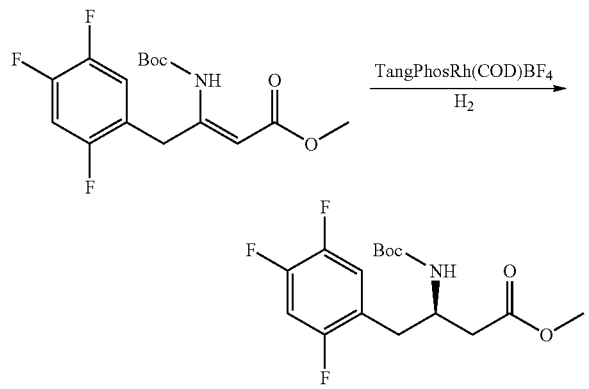

1.28 g (3.71 mmol) of (Z)-Methyl-3-[N-(tert-butoxycarbonyl)amino]-4-(2,4,5-trifluorophenyl)but-2-enoate of Example 3, 2.2 mg TangPhosRh(COD)BF₄ and 10 mL THF were charged to a pressure bomb under N₂ atmosphere. The N₂ atmosphere was replaced by H₂ (10 bars). The mixture was stirred at rt for 18 h. The reaction solution was passed through a silica gel pad and evaporated to dryness. The reaction gave quantitative yield and 99.0% ee. ¹H NMR (300 MHz, CDCl₃) 7.10-7.00 (m, 1H), 6.95-6.85 (m, 1H), 5.10 (m, 1H), 4.20-4.10 (m, 1H), 3.70 (s, 3H), 2.85 (m, 1H), 2.60-2.50 (m, 1H), 1.39 (s, 9H)

Example 5

(R)-3-[N-(tert-butoxycarbonyl)amino]-4-(2,4,5-trifluorophenyl)butanoic acid

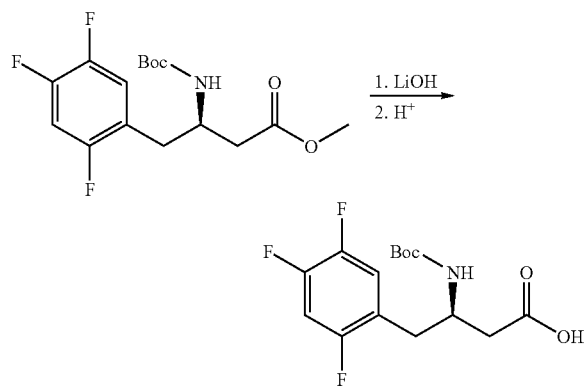

To a solution of (R)-Methyl-3-[N-(tert-butoxycarbonyl)amino]-4-(2,4,5-tri-fluorophenyl)butanoate of Example 4 (1.28 g, 3.69 mmol) in 15 mL THF and 15 mL water was added 3 equiv. LiOH.H₂O. The reaction mixture was stirred for 16 h. 10 ml saturated NaHCO₃ was added. THF was evaporated and the aq solution was acidified to pH 2-3 with NaHSO₄, then extracted by ethyl acetate (3×15 mL). The combined organic phase was washed with brine and dried over Na₂SO₄. Concentration in vacuo afforded 1.17 g of white solid (95.1%). ¹H NMR (300 MHz, CD3OD) 7.13-7.03 (m, 2H), 4.20-4.10 (m, 1H), 3.00-2.90 (m, 1H), 2.75-2.60 (m, 1H), 2.45-2.55 (m, 2H), 1.35 (s, 9H)

Example 6

(Z)-Methyl-3-N-acetylamino-4-(2,4,5-trifluorophenyl)but-2-enoate

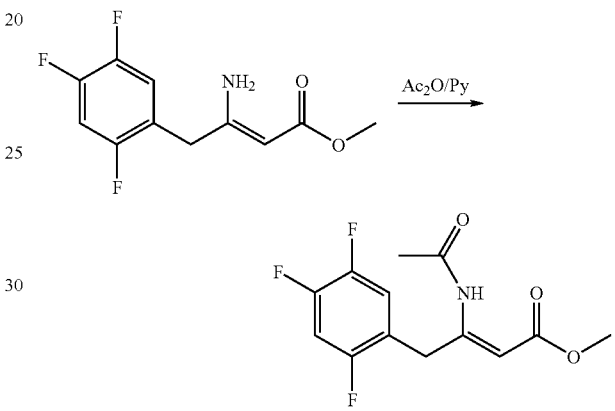

A solution of (Z)-methyl-3-amino-4-(2,4,5-trifluorophenyl)but-2-enoate (4.90 g, 20 mmol) of Example 2, pyridine (4.8 ml) and acetic anhydride (4.80 g, mmol) in THF (30 ml) was heated to reflux for 16 h. The reaction mixture was stirred at room temperature, quenched with 1N HCl, and extracted with ethyl acetate (3×20 ml). The combined organic phase was washed with saturated sodium bicarbonate, then brine, then dried over sodium sulfate. Concentration was followed by purification by flash chromatography to afford 4.03 g of product (70.3%). ¹H NMR (300 MHz, CDCl₃) 11.14 (s, 1H) 7.10-7.00 (m, 1H), 6.96-6.87 (m, 1H), 4.81 (s, 1H), 4.14 (s, 2H), 3.70 (s, 3H), 2.14 (s, 3H).

Example 7

(R)-Methyl-3-N-acetylamino-4-(2,4,5-trifluorophenyl)butanoate

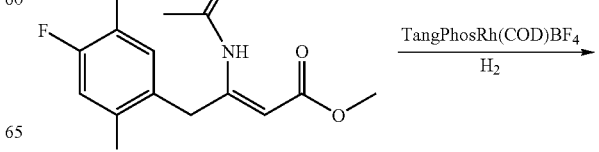

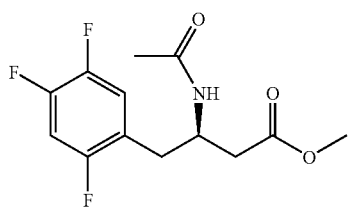

2.30 g (8.01 mmol) of (Z)-Methyl-3-[N-(tert-butoxycarbonyl)amino]-4-(2,4,5-trifluorophenyl)but-2-enoate of Example 6, 4.6 mg TangPhosRh(COD)BF₄ and 20 ml THF were charged to a pressure bomb under N₂ atmosphere. The N₂ atmosphere was replaced by H₂ (10 bars). The mixture was stirred at rt for 18 h. The reaction solution evaporated to dryness to give quantitative yield and 97.0% ee. ¹H NMR (300 MHz, CDCl₃) 7.08-7.02 (m, 1H), 7.00-6.87 (m, 1H), 6.25-6.23 (m, 1H), 4.50-4.35 (m, 1H), 3.70 (s, 3H), 2.90-2.80 (m, 2H), 2.62-2.42 (m, 2H), 1.92 (s, 3H)

Example 8

(R)-3-[N-(tert-butoxycarbonyl)amino]-4-(2,4,5-trifluorophenyl)butanoic acid

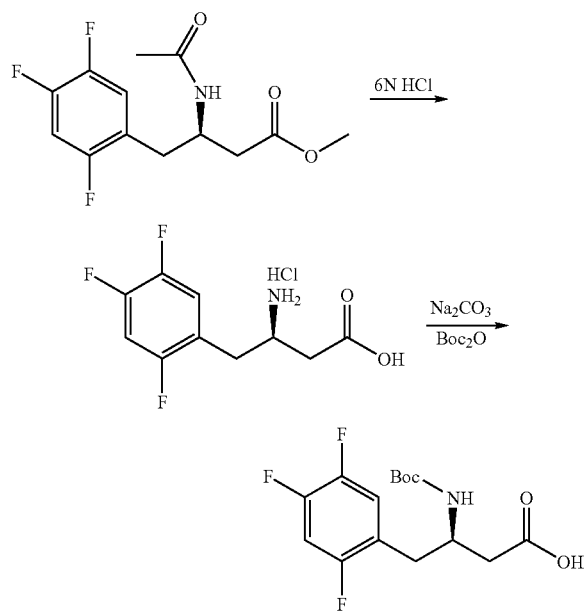

A suspension of (R)-Methyl-3-N-acetylamino-4-(2,4,5-trifluorophenyl) butanoate of Example 7 in 6N HCl was heated to reflux overnight. The clear solution was evaporated to dryness and the residue was dissolved in sodium carbonate solution (0.85 g in 20 ml H₂O). To this solution was added Boc₂O (1.92 g, 8.81 mmol) in THF (20 ml) dropwise at 0° C. with stirring. The mixture was warmed to room temperature with stirring for 1 h. THF was evaporated and the aq solution was acidified to pH 2-3 with NaHSO₄, then extracted by ethyl acetate (3×15 ml). The combined organic phase was washed with brine and dried over Na₂SO₄. Concentration in vacuo afforded 2.32 g of white solid (86.9%). ¹H NMR (300 MHz, CD₃OD) 7.13-7.03 (m, 2H), 4.20-4.10 (m, 1H), 3.00-2.90 (m, 1H), 2.75-2.60 (m, 1H), 2.45-2.55 (m, 2H), 1.35 (s, 9H)

Example 9

(R)-tert-Butyl-4-oxo-4-[3-(trifluoromethyl)-5,6-dihydro[1,2,4]triazolo[4,3-a]pyrozin-7(8H)-yl]-1-(2,4,5-trifluorophenyl)-butan-2-yl carbamate

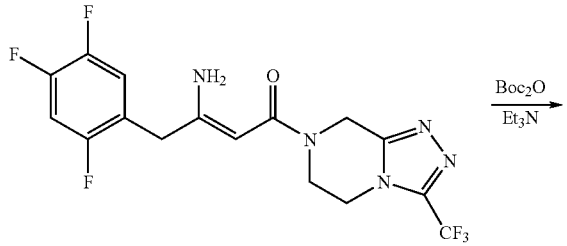

To a solution of (R)-3-[N-(tert-butoxycarbonyl)amino]-4-(2,4,5-trifluoro-phenyl)butanoic acid (0.333 g, 1 mmol) of Example 8 and 3-(trifluoromethyl-5,6,7,8-tetrahydro-1,2,4-triazolo[4,3a]pyrozine (0.192 g, 1 mmol) in DMF (12 ml) was added HOBT (0.162 g, 1.2 mmol) and EDC (0.230 g. 1.2 mmol) at 0° C. After being stirred at room temperature for 16 h, DMF was evaporated and the residue extracted with ethyl acetate (3×20 ml). The organic extracts were washed with NaHSO₄ aq, then NaHCO₃, then brine, and then dried over Na₂SO₄. Concentration was followed by purification by flash chromatography to afford 0.375 g of the title compound (71.8%). ¹H NMR (300 MHz, CDCl₃) 7.10-7.00 (m, 1H), 7.00-6.90 (m, 1H), 5.25-5.35 (br, 1H), 5.10-5.00 (m, 1H), 4.90 (s, 1H), 4.30-3.90 (m, 5H), 3.00-2.90 (m, 2H), 2.80-2.60 (m, 2H), 1.35 (s, 9H)

Example 10

(Z)-tert-Butyl-4-oxo-4-[3-(trifluoromethyl)-5,6-dihydro[1,2,4]triazolo[4,3-a]pyrozin-7(8H)-yl]-1-(2,4,5-trifluorophenyl)-but-2-en-2-yl carbamate -continued

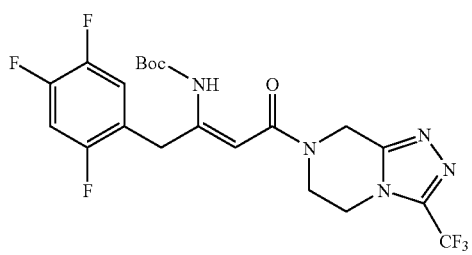

To a solution of (Z)-4-oxo-4-[3-(trifluoromethyl)-5,6-dihydro[1,2,4]triazolo[4,3-a]pyrozin-7(8H)-yl]-1-(2,4,5-trifluorophenyl)-but-2-en-2-amine (2.00 g, 4.94 mmol) and triethyl amine (1.00 g, 9.88 mmol) in dichloromethene (100 mL) was added Boc anhydride (2.15 g, 9.85 mmol). The reaction mixture was stirred at reflux for 40 h. Concentration was followed by purification by flash chromatography to afford 1.24 g of product (49.8%). $^1$H NMR (400 MHz, d6-DMSO) 11.27 (s, 1H) 7.56-7.50 (m, 1H), 5.63 (s, 1H), 5.00-4.94 (m, 2H), 4.06-4.00 (m, 4H), 1.35 (s, 9H).

Example 11

(R)-tert-Butyl-4-oxo-4-[3-(trifluoromethyl)-5,6-dihydro[1,2,4]triazolo[4,3-a]pyrozin-7(8H)-yl]-1-(2,4,5-trifluorophenyl)-butan-2-yl carbamate

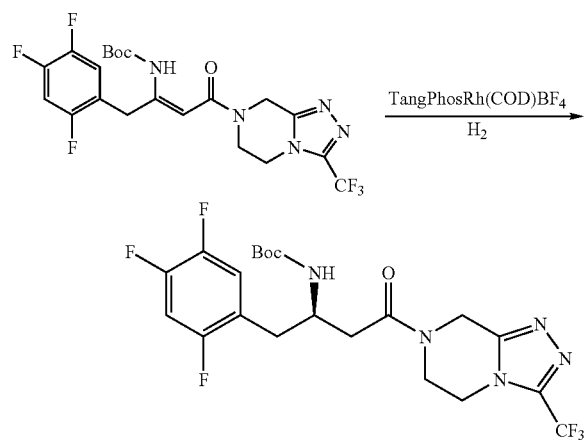

0.10 g (0.20 mmol) of Z)-tert-Butyl-4-oxo-4-[3-(trifluoromethyl)-5,6-dihydro[1,2,4]triazolo[4,3-a]pyrozin-7(8H)-yl]-1-(2,4,5-trifluorophenyl)-but-2-en-2-yl carbamate of Example 10, 5.7 mg of TangPhosRh(COD)BF$_4$ and 5.0 ml trifluoroethanol were charged to a pressure bomb under N$_2$ atmosphere. The N$_2$ atmosphere was replaced by H$_2$ (50 bars). The mixture was stirred at 90° C. for 16 h. The reaction solution evaporated to dryness to give quantitative yield and 37.7% ee.

Example 12

(R)-tert-Butyl-4-oxo-4-[3-(trifluoromethyl)-5,6-dihydro[1,2,4]triazolo[4,3-a]pyrozin-7(8H)-yl]-1-(2,4,5-trifluorophenyl)-butan-2-yl carbamate

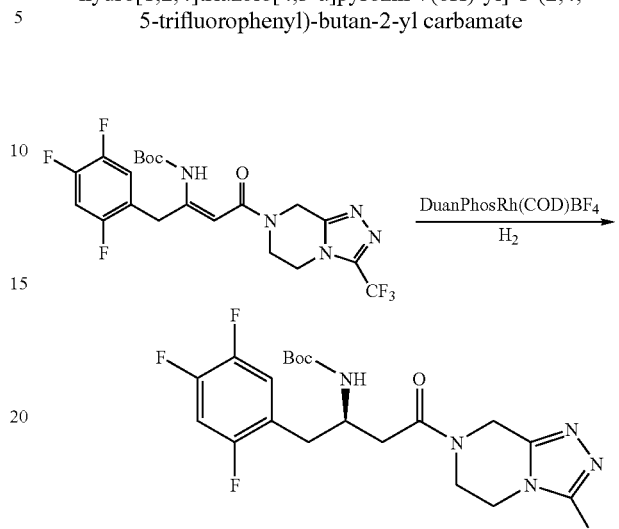

0.10 g (0.20 mmol) of (Z)-tert-Butyl-4-oxo-4-[3-(trifluoromethyl)-5,6-dihydro[1,2,4]triazolo[4,3-a]pyrozin-7(8H)-yl]-1-(2,4,5-trifluorophenyl)-but-2-en-2-yl carbamate of Example 10, 6.7 mg of (Sp,Rc)-DuanPhosRh(COD)BF$_4$ and 5.0 ml trifluoroethanol were charged to a pressure bomb under N$_2$ atmosphere. The N$_2$ atmosphere was replaced by H$_2$ (50 bars). The mixture was stirred at 90° C. for 16 h. The reaction solution evaporated to dryness to give quantitative yield and 44.2% ee.

Example 13

(R)-4-Oxo-4-[3-(trifluoromethyl)-5,6-dihydro[1,2,4]triazolo[4,3-a]pyrozin-7(8H)-yl]-1-(2,4,5-trifluorophenyl)butan-2-amine hydrochloride

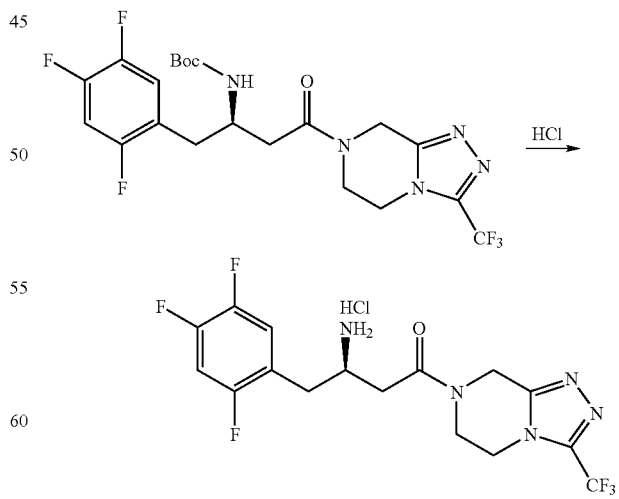

To a solution of the tert-butyl{(1R)-3-oxo-1-(2,4,5)-trifluorobenzyl}-3-[3-(tri-fluoromethyl)-5,6-dihydro[1,2,4]triazolo[4,3-a]pyrozin-7(8H)-yl]propyl}carbamate (0.193 mg) of Example 9 in methanol was added 20 ml of saturated hydrochloride solution in methanol. After the reaction completed, the solution was concentrated to afford white solid. $^1$H NMR (300 MHz, CD$_3$OD) 7.50-7.30 (m, 1H), 7.30-7.15 (m, 1H) 5.05 (m, 2H) 4.50-3.75 (m, 5H), 3.20-2.80 (m, 4H).

While the invention has been disclosed in connection with the preferred embodiments and methods of use, it is to be understood that many alternatives, modifications, and variations thereof are possible without departing from the present invention. Thus, the present invention is intended to embrace all such alternatives, modifications, and variations as may be apparent to those skilled in the art and encompassed within the hereinafter appended claims.

What is claimed is:

1. A process for producing an enantiomerically enriched compound having the structure of Formula I:

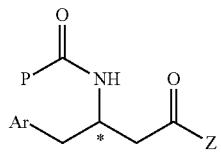

wherein the R-configuration, or S-configuration at the stereogenic center is marked with an *; which process comprises the step of hydrogenating an enamide compound having the structure of formula III:

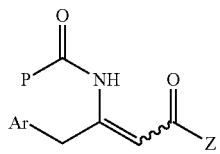

in an organic solvent in the presence of a catalyst comprising a transition metal selected from the group consisting of rhodium and iridium, complexed to a chiral diphosphine ligand;
  wherein Ar is phenyl which is unsubstituted or substituted with one to five substituents independently selected from the group consisting of halogen, trifluoromethyl, and trifluoromethoxy;
  Z is OR$^1$, SR$^1$ or NR$^1$R$^2$; and P is R$^3$, OR$^3$ or NR$^3$R$^4$;
  R$^1$ and R$^2$ are each independently selected from the group consisting of H, C$_{1-8}$ alkyl, C$_{5-12}$ cycloalkyl, aryl and aryl-C$_{1-2}$-alkyl; or R$^1$ and R$^2$ together with the nitrogen atom to which they are attached form a C$_{4-7}$-member heterocyclic ring system optionally containing an additional heteroatom selected from O, S, and N—C$_{1-4}$-alkyl, said heterocyclic ring system being optionally fused with a 5- to 6-member saturated, unsaturated or aromatic carbocyclic ring system or a 5- to 6-member saturated, unsaturated or aromatic heterocyclic ring system containing one to two heteroatoms selected from O, S, and N—C$_{1-4}$-alkyl, said fused ring system being unsubstituted or substituted with one to two substituents independently selected from the group consisting of hydroxy, amino, fluoro, C$_{1-4}$ alkyl, C$_{1-4}$ alkoxy and trifluoromethyl; and
  R$^3$ and R$^4$ are each independently selected from the group consisting of H, C$_{1-8}$ alkyl, aryl, C$_{5-12}$ cycloalkyl and aryl-C$_{1-2}$-alkyl; or R$^3$ and R$^4$ together with the nitrogen atom to which they are attached form a C$_{4-7}$-member heterocyclic ring system optionally containing an additional heteroatom selected from O, S, and N—C$_{1-4}$-alkyl.

2. The process of claim 1 wherein the transition metal catalyst comprises [M(1,5-cyclooctadiene)$_2$]X or [M(norbornadiene)$_2$]X, wherein X is a noncoordinating anion selected from the group consisting of methanesulfonate, trifluoromethanesulfonate, tetrafluoroborate, hexafluorophosphate and hexafluoroantimonate; and M is rhodium or iridium.

3. The process of claim 1, wherein said catalyst may be preformed or generated in situ, and is represented by the formula:

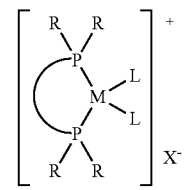

wherein X$^-$ is a non-coordinating anion selected from the group consisting of methanesulfonate trifluoromethanesulfonate, tetrafluoroborate, hexafluorophosphate and hexafluoroantimonate; L is a chelating diolefin selected from 1,5-cyclooctadiene or norbornadiene; M is rhodium or iridium; P is phosphorus; and each R is independently selected from the group consisting of C$_{1-8}$ alkyl, C$_{3-8}$ cycloalkyl and aryl.

4. The process of claim 1 wherein Ar is 2,4,5-trifluorophenyl, or 2,5-difluorophenyl.

5. The process of claim 1 wherein P is R$^3$.

6. The process of claim 5 wherein R$^3$ is H, C$_{1-8}$ alkyl or aryl.

7. The process of claim 1 wherein P is OR$^3$.

8. The process of claim 7 wherein R$^3$ is tert-butyl or benzyl.

9. The process of claim 1 wherein Z is SR$^1$ or NR$^1$R$^2$.

10. The process of claim 9 wherein NR$^1$R$^2$ is a heterocycle with the structure of Formula VI:

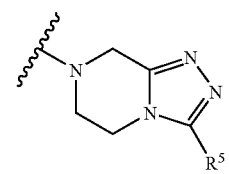

wherein R$^5$ is H, C$_{1-4}$ alkyl or trifluoromethyl.

11. The process of claim 10 wherein said R$^5$ is trifluoromethyl.

12. The process of claim 1 wherein said chiral diphosphine ligand is selected from the following compounds:

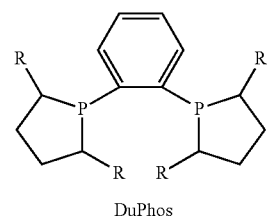

DuPhos

-continued

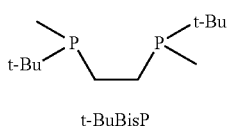
t-BuBisP

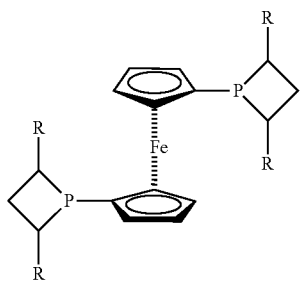
FerroTANE

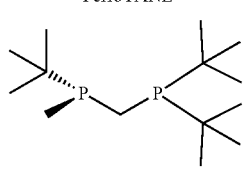
TrichickenfootPhos

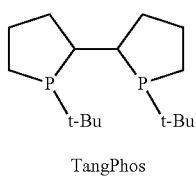
TangPhos

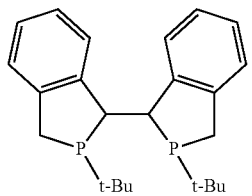
DuanPhos

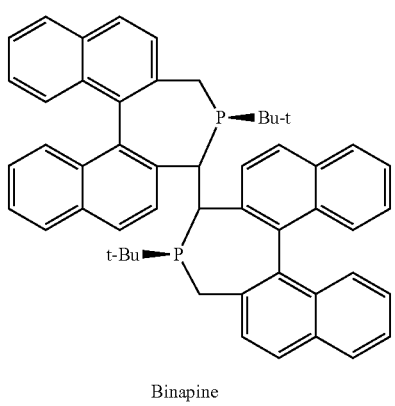
Binapine

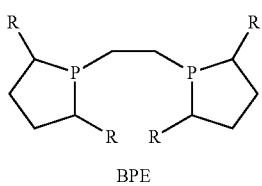
BPE

-continued

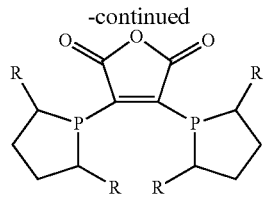
MalPhos

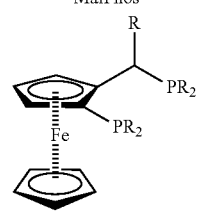
Josiphos

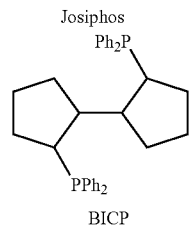
BICP wherein each R is independently $C_{1-8}$ alkyl, $C_{3-8}$ cycloalkyl or aryl; and P is phosphorus.

13. The process of claim 12, wherein said chiral diphosphine ligand is selected from the group consisting of TangPhos and DuanPhos.

14. A process for producing an enantiomerically enriched compound having the structure of Formula I:

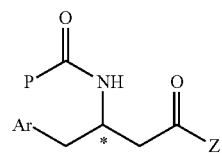

I wherein the R-configuration, or S-configuration at the stereogenic center is marked with an *; which process comprises the steps of:

(i) reacting a compound having the structure of Formula V:

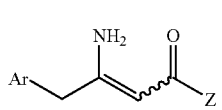

V with an acylation reagent in the presence of an organic base in an organic solvent, to form an enamide compound having the structure of Formula III:

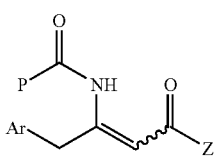

III wherein said acylation reagent is selected from the group consisting of $C_{2-8}$ alkyl-, aryl- and aryl-$C_{1-2}$-alkyl-acyl chlorides, anhydrides and chloroformates;
and
(ii) hydrogenating said enamide compound in an organic solvent in the presence of a catalyst comprising a transition metal selected from the group consisting of rhodium and iridium, complexed to a chiral diphosphine ligand;
wherein Ar is phenyl which is unsubstituted or substituted with one to five substituents independently selected from the group consisting of halogen, trifluoromethyl, and trifluoromethoxy;
Z is $OR^1$, $SR^1$ or $NR^1R^2$; and P is $R^3$, $OR^3$ or $NR^3R^4$;
$R^1$ and $R^2$ are each independently selected from the group consisting of H, $C_{1-8}$ alkyl, $C_{5-12}$ cycloalkyl, aryl and aryl-$C_{1-2}$-alkyl; or $R^1$ and $R^2$ together with the nitrogen atom to which they are attached form a $C_{4-7}$-member heterocyclic ring system optionally containing an additional heteroatom selected from O, S, and N—$C_{1-4}$-alkyl, said heterocyclic ring system being optionally fused with a 5- to 6-member saturated, unsaturated or aromatic carbocyclic ring system or a 5- to 6-member saturated, unsaturated or aromatic heterocyclic ring system containing one to two heteroatoms selected from O, S, and N—$C_{1-4}$-alkyl, said fused ring system being unsubstituted or substituted with one to two substituents independently selected from the group consisting of hydroxy, amino, fluoro, $C_{1-4}$ alkyl, $C_{1-4}$ alkoxy and trifluoromethyl; and
$R^3$ and $R^4$ are each independently selected from the group consisting of H, $C_{1-8}$ alkyl, aryl, $C_{5-12}$ cycloalkyl and aryl-$C_{1-2}$-alkyl; or $R^3$ and $R^4$ together with the nitrogen atom to which they are attached form a $C_{4-7}$-member heterocyclic ring system optionally containing an additional heteroatom selected from O, S, and N—$C_{1-4}$-alkyl.

15. The process of claim 14, wherein said catalyst may be preformed or generated in situ, and is represented by the formula:

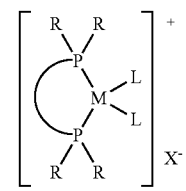

wherein $X^-$ is a non-coordinating anion selected from the group consisting of methanesulfonate trifluoromethanesulfonate, tetrafluoroborate, hexafluorophosphate and hexafluoroantimonate; L is a chelating diolefin selected from 1,5-cyclooctadiene or norbornadiene; M is rhodium or iridium; P is phosphorus; and each R is independently selected from the group consisting of $C_{1-8}$ alkyl, $C_{3-8}$ cycloalkyl and aryl.

16. The process of claim 14 wherein said acylation reagent is acetyl chloride, acetic anhydride, tert-butoxycarbonyl anhydride or benzyl chloroformate.

* * * * *

UNITED STATES PATENT AND TRADEMARK OFFICE
CERTIFICATE OF CORRECTION

| | | |
|---|---|---|
| PATENT NO. | : 8,278,486 B2 | Page 1 of 2 |
| APPLICATION NO. | : 12/650128 | |
| DATED | : October 2, 2012 | |
| INVENTOR(S) | : Shulin Wu et al. | |

It is certified that error appears in the above-identified patent and that said Letters Patent is hereby corrected as shown below:

In the Claims:

At column 18, line 38, please delete the following from claim 9:

"$SR^1$"

and replace it with

--$OR^1$--, so that the claim reads:

9. The process of claim 1 wherein Z is $OR^1$ or $NR^1R^2$.

At column 18, lines 39-52, please delete dependent claim 10, and replace it with the following independent claim:

--Claim 10.   A process for producing an enantiomerically enriched compound having the structure of Formula I:

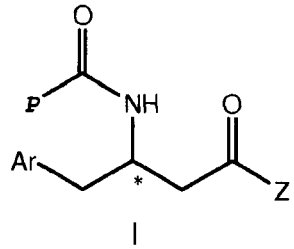

wherein the R-configuration, or S-configuration at the stereogenic center is marked with an *;
which process comprises the step of hydrogenating an enamide compound having the structure of formula III:

Signed and Sealed this
Twenty-second Day of January, 2013

David J. Kappos
*Director of the United States Patent and Trademark Office*

CERTIFICATE OF CORRECTION (continued)
U.S. Pat. No. 8,278,486 B2

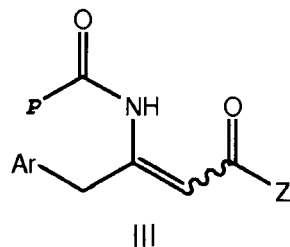

III in an organic solvent in the presence of a catalyst comprising a transition metal selected from the group consisting of rhodium and iridium, complexed to a chiral diphosphine ligand;

wherein Ar is phenyl which is unsubstituted or substituted with one to five substituents independently selected from the group consisting of halogen, trifluoromethyl, and trifluoromethoxy;

$P$ is $R^3$, $OR^3$ or $NR^3R^4$; wherein $R^3$ and $R^4$ are each independently selected from the group consisting of H, $C_{1-8}$ alkyl, aryl, $C_{5-12}$ cycloalkyl and aryl-$C_{1-2}$-alkyl; or $R^3$ and $R^4$ together with the nitrogen atom to which they are attached form a $C_{4-7}$-member heterocyclic ring system optionally containing an additional heteroatom selected from O, S, and N-$C_{1-4}$-alkyl; and Z is $NR^1R^2$ wherein $NR^1R^2$ is a heterocycle with the structure of Formula VI:

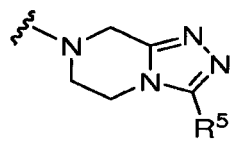

VI wherein $R^5$ is H, $C_{1-4}$ alkyl or trifluoromethyl.--